US 12,376,889 B2

(12) United States Patent
Linares (10) Patent No.: US 12,376,889 B2
(45) Date of Patent: Aug. 5, 2025

(54) EXPANDABLE SPRING STEPPED IN JACK FOR INSTALLATION BETWEEN UPPER AND LOWER SUCCEEDING ARTICULAR PROCESSES

(71) Applicant: Linares Spinal Devices, LLC, Auburn Hills, MI (US)

(72) Inventor: Miguel A. Linares, Bloomfield Hills, MI (US)

(73) Assignee: Linares Spinal Devices, LLC, Auburn Hills, MI (US)

( * ) Notice: Subject to any disclaimer, the term of this patent is extended or adjusted under 35 U.S.C. 154(b) by 130 days.

(21) Appl. No.: 18/082,642

(22) Filed: Dec. 16, 2022

(65) Prior Publication Data

US 2023/0240726 A1    Aug. 3, 2023

Related U.S. Application Data

(60) Provisional application No. 63/304,094, filed on Jan. 28, 2022.

(51) Int. Cl.
*A61B 17/70* (2006.01)
*A61B 17/00* (2006.01)

(52) U.S. Cl.
CPC ...... *A61B 17/7065* (2013.01); *A61B 17/7047* (2013.01); *A61B 2017/00407* (2013.01)

(58) Field of Classification Search
CPC ............ A61B 17/7065; A61B 17/7047; A61B 2017/00407; A61B 17/7062; A61B 17/7064; A61B 17/7067; A61B 17/707; A61B 17/8004; A61B 17/8009; A61B 17/8023; A61F 2002/30505; A61F 2002/30492; A61F 2002/30494; A61F 2002/30487; A61F 2/4405; Y10T 403/32483; Y10T 403/32524

See application file for complete search history.

(56) References Cited

U.S. PATENT DOCUMENTS

| | | | | |
|---|---|---|---|---|
| 5,810,815 A | * | 9/1998 | Morales | A61B 17/7055 606/261 |
| 5,928,231 A | * | 7/1999 | Klein | A61B 17/74 606/305 |
| 6,932,820 B2 | * | 8/2005 | Osman | A61B 17/8009 606/282 |

(Continued)

*Primary Examiner* — Lynnsy M Summitt
(74) *Attorney, Agent, or Firm* — Dinsmore & Shohl LLP (57) ABSTRACT

A spinal jack adapted for installation between first and second vertebral processes and including an upper spinal jack body and a lower spinal jack body having gripping portions adapted for engaging the vertebral processes. A pair of upwardly extending sleeves are integrated into the lower spinal body and coaxially receive a pair of downwardly extending stems integrated into the upper spinal body. A pair of spring actuated and stepped pins are incorporated into the lower jack body and, when inwardly actuated, engage recessed locations configured along the stems in order to define an adjusted separation distance between the bodies. In a second variant, a rotatable gear is incorporated into one of the bodies and engages a pair of outer beveled gears, with additional gears actuated by the outer bevel gears and in turn engaging any of opposing teeth or threads configured into the extending stems in order to define an adjusted separation distance between the bodies.

5 Claims, 7 Drawing Sheets

(56) References Cited

U.S. PATENT DOCUMENTS

| | | | |
|---|---|---|---|
| 7,238,204 B2* | 7/2007 | Le Couedic | A61B 17/7062 623/17.11 |
| 7,763,056 B2* | 7/2010 | Dalton | A61B 17/7059 606/280 |
| 7,842,908 B2 | 11/2010 | Andresson et al. | |
| 8,048,118 B2* | 11/2011 | Lim | A61B 17/7062 606/248 |
| 8,328,848 B2* | 12/2012 | Lowery | A61F 2/442 606/248 |
| 8,328,871 B2 | 12/2012 | Capote et al. | |
| 8,357,181 B2* | 1/2013 | Lange | A61F 2/30 606/248 |
| 8,545,563 B2 | 10/2013 | Brun et al. | |
| 8,574,267 B2* | 11/2013 | Linares | A61F 2/442 606/248 |
| 8,585,738 B2* | 11/2013 | Linares | A61B 17/8605 606/248 |
| 8,623,056 B2 | 1/2014 | Linares | |
| 9,005,248 B2* | 4/2015 | Taber | A61F 2/4405 606/249 |
| 9,023,108 B2 | 5/2015 | Hansell et al. | |
| 9,144,503 B2 | 9/2015 | Stinchfield et al. | |
| 9,339,298 B1* | 5/2016 | Morales Chavarria | A61B 17/7023 |
| 9,468,703 B2* | 10/2016 | Khanna | A61L 31/04 |
| 9,554,831 B2* | 1/2017 | McKay | A61B 17/7068 |
| 9,655,738 B2 | 5/2017 | Stinchfield et al. | |
| 9,833,262 B2 | 12/2017 | Lim et al. | |
| 10,076,421 B2 | 9/2018 | Dewey | |
| 10,245,081 B2* | 4/2019 | Arnin | A61B 17/8019 |
| 11,039,859 B2 | 6/2021 | Simpson et al. | |
| 11,154,335 B2* | 10/2021 | Arnin | A61B 17/7071 |
| 11,432,937 B1* | 9/2022 | Linares | A61F 2/30749 |
| 11,896,268 B2* | 2/2024 | Linares | A61F 2/4405 |
| 11,951,015 B2* | 4/2024 | Linares | A61F 2/4405 |
| 12,011,360 B2* | 6/2024 | Linares | A61F 2/4405 |
| 12,137,947 B2* | 11/2024 | Linares | A61B 17/7062 |
| 2003/0114856 A1* | 6/2003 | Nathanson | A61B 17/8009 606/70 |
| 2005/0034573 A1* | 2/2005 | Hsien | B25B 13/461 81/177.2 |
| 2006/0293662 A1* | 12/2006 | Boyer, II | A61B 17/1671 606/249 |
| 2007/0100340 A1* | 5/2007 | Lange | A61B 17/7065 606/279 |
| 2008/0015577 A1* | 1/2008 | Loeb | A61B 17/7059 606/330 |
| 2008/0058808 A1* | 3/2008 | Klyce | A61B 17/7056 606/279 |
| 2009/0306717 A1* | 12/2009 | Kercher | A61B 17/7011 606/279 |
| 2010/0004697 A1* | 1/2010 | Fortin | A61B 17/66 606/86 R |
| 2010/0016969 A1 | 1/2010 | Richter et al. | |
| 2011/0015747 A1 | 1/2011 | McManus et al. | |
| 2011/0251692 A1 | 10/2011 | McLaughlin et al. | |
| 2011/0264144 A1* | 10/2011 | Arthur | A61B 17/8004 606/246 |
| 2012/0109204 A1* | 5/2012 | Linares | A61F 2/442 606/249 |
| 2017/0143384 A1 | 5/2017 | Hutton et al. | |
| 2017/0216051 A1 | 8/2017 | Dewey | |
| 2017/0290671 A1 | 10/2017 | Milz et al. | |
| 2020/0229936 A1 | 7/2020 | Milz et al. | |
| 2021/0052307 A1 | 2/2021 | Soo et al. | |
| 2023/0240726 A1* | 10/2023 | Linares | A61B 17/7065 606/249 |
| 2023/0320864 A1* | 10/2023 | Linares | A61F 2/4611 606/247 |

* cited by examiner

EXPANDABLE SPRING STEPPED IN JACK FOR INSTALLATION BETWEEN UPPER AND LOWER SUCCEEDING ARTICULAR PROCESSES

CROSS REFERENCE TO RELATED APPLICATIONS

The present application claims the priority of U.S. Ser. No. 63/304,094 filed Jan. 28, 2022.

FIELD OF THE INVENTION

The present invention relates generally to spinal jacks for providing inter-vertebral support. More specifically, the present invention teaches an adjustable spinal jack for installation between superior articular processes of upper and lower succeeding vertebrae.

BACKGROUND OF THE INVENTION

Spinal jacks designs are known in the prior art for providing adjusted and secure positioning support between succeeding spinal vertebra. Examples of these are depicted in each of Linares U.S. Pat. No. 8,623,056 and Linares U.S. Pat. No. 8,585,738.

SUMMARY OF THE PRESENT INVENTION

The present invention discloses a spinal jack adapted for installation between first and second vertebral processes and, in a first embodiment, includes an upper spinal jack body and a lower spinal jack body. Each of the bodies includes gripping portions adapted for engaging the vertebral processes. A pair of upwardly extending sleeves integrated into the lower spinal body and coaxially receiving a pair of downwardly extending stems integrated into the upper spinal body. A pair of spring actuated and stepped pins are incorporated into the lower jack body and, when inwardly actuated, engage recessed locations configured along the stems in order to define an adjusted separation distance between the bodies.

The gripping portions each further include a pocket adapted to receive the vertebral process therebetween. The pockets each further include textured surfaces for providing additional gripping of the vertebral processes.

The upper and lower bodies further include any medical grade sanitary metal, plastic or composite material. The gripping portions further include a substantially "U" shape with aligning apertures configured in spaced apart and extending legs for receiving screw fasteners for securing the gripping portions to the vertebral processes.

One or more outward biasing springs are seated within pockets in the lower body for upwardly displacing the stems and upper jack body. A tool bit is engageable with a bit receiving location of the central gear accessible through an inlet aperture defined in the body.

In a second variant, a rotatable gear incorporated into one of the bodies and engaging a pair of outer beveled gears. Additional gears are actuated by the outer bevel gears and in turn engage any of opposing teeth or threads configured into the extending stems in order to define an adjusted separation distance between the bodies.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

With reference to the attached illustrations, the present invention discloses an adjustable spinal jack for installation between superior articular processes of upper and lower succeeding vertebrae. A general representation of a selected jack is depicted generally at 10 in a retracted position in FIG. 1, and is further shown in each of succeeding FIGS. 2-3 positioned between upper 2 and lower 4 successive superior articular processes corresponding to upper and lower vertebrae.

The present invention provides an expandable spinal jack, which overcomes many of the disadvantages of the prior art and provides an effective solution for stabilizing and fixing in position a given orientation established between the succeeding vertebrae. As will be further described, the spinal jack designs described herein further permit adjustment, at any future time following initial surgical implantation, in a minimally invasive fashion and in order to re-adjust the spatial positioning established between the upper and lower separable halves or sections, such as in order to compensate and correct for future/downstream vertebral complications following the initial implantation of the spinal jack.

Referring again to FIG. 1, the perspective view of the spinal jack according to one non-limiting variant includes first 12 and second 14 bodies, also hereinafter referred to as spinal jack halves, which are shown in a retracted position prior to being installed between succeeding superior articular processes associated with upper and lower consecutive spinal vertebra. Each of the spinal jack halves can be constructed of a suitable medical grade sanitary metal, plastic or composite and can incorporate opposite and outwardly facing gripping portions, these as further shown exhibiting a substantially "U" shape with aligning apertures configured in spaced apart and extending legs (see pairs 16/18 for each of a first or lower jack half 12 and further at 20/22 for second or upper half 14).

Figure 1:
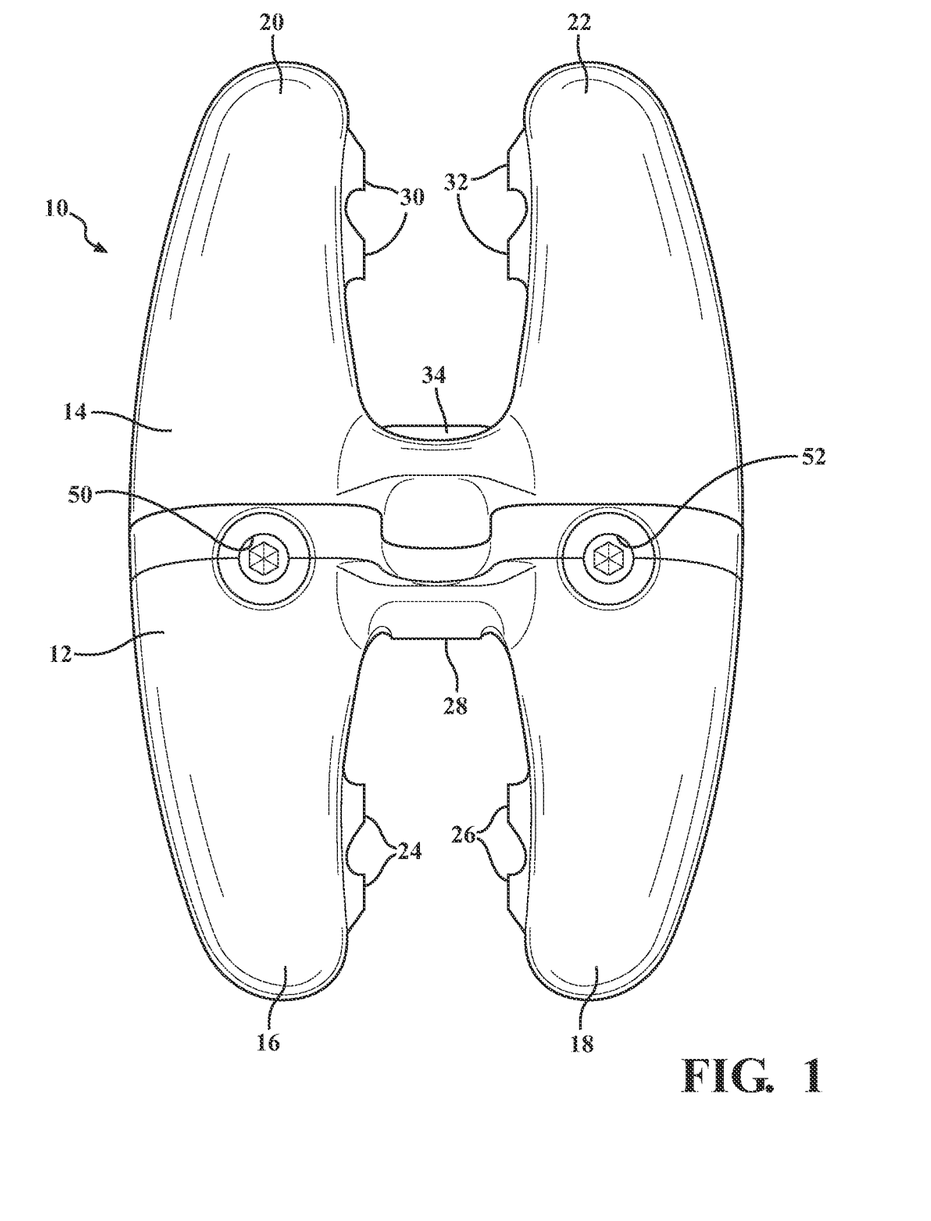
FIG. 1 is a perspective view of a spring stepped pin jack according to one non-limiting variant and having first and second spinal jack halves shown in a retracted position prior to being installed between succeeding superior articular processes associated with upper and lower consecutive spinal vertebra.

As understood, the spaced apart pairs of legs 16/18 and 20/22 of the opposite extending gripping portions are adapted to seat the upper and lower consecutive superior articular processes, The inner "U" shaped surface profile of each of the gripping portions is further exhibited by any type of textured or ribbed profile (see at inner side surfaces 24/26 and interconnecting base surface 28 for the lower spinal jack gripping portion as well as inner side surfaces 30/32 and interconnecting base surface 34 for the upper spinal jack gripping portion) the purpose of which is to provide additional resistive engagement against the facet surfaces of the vertebral processes.

Although not shown it is envisioned that any type of screw fasteners can be employed and which, upon positioning the gripping portions in contact with the articular processes, can be drilled through the vertebral processes in order to anchor the spinal jack halves to the respective vertebrae. Alternatively, the construction of the spinal jack halves is such that the gripping portions can be compressed and crimped into engagement against the opposing sides of the vertebral processes without the use of separate screws.

Figure 3:
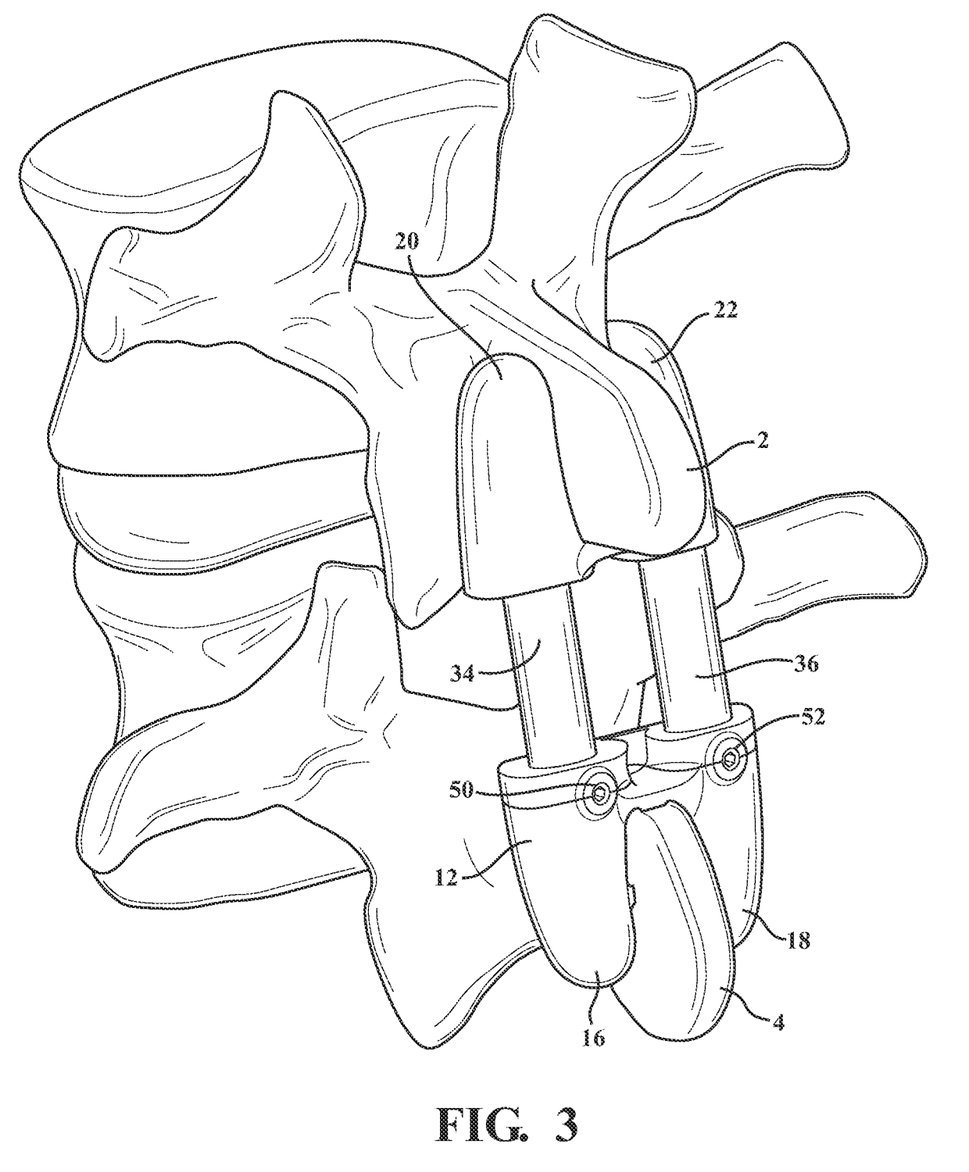
FIG. 3 is a succeeding view to FIG. 2 and depicting the spinal jack in an expanded position for properly orienting the vertebrae.
Figure 4:
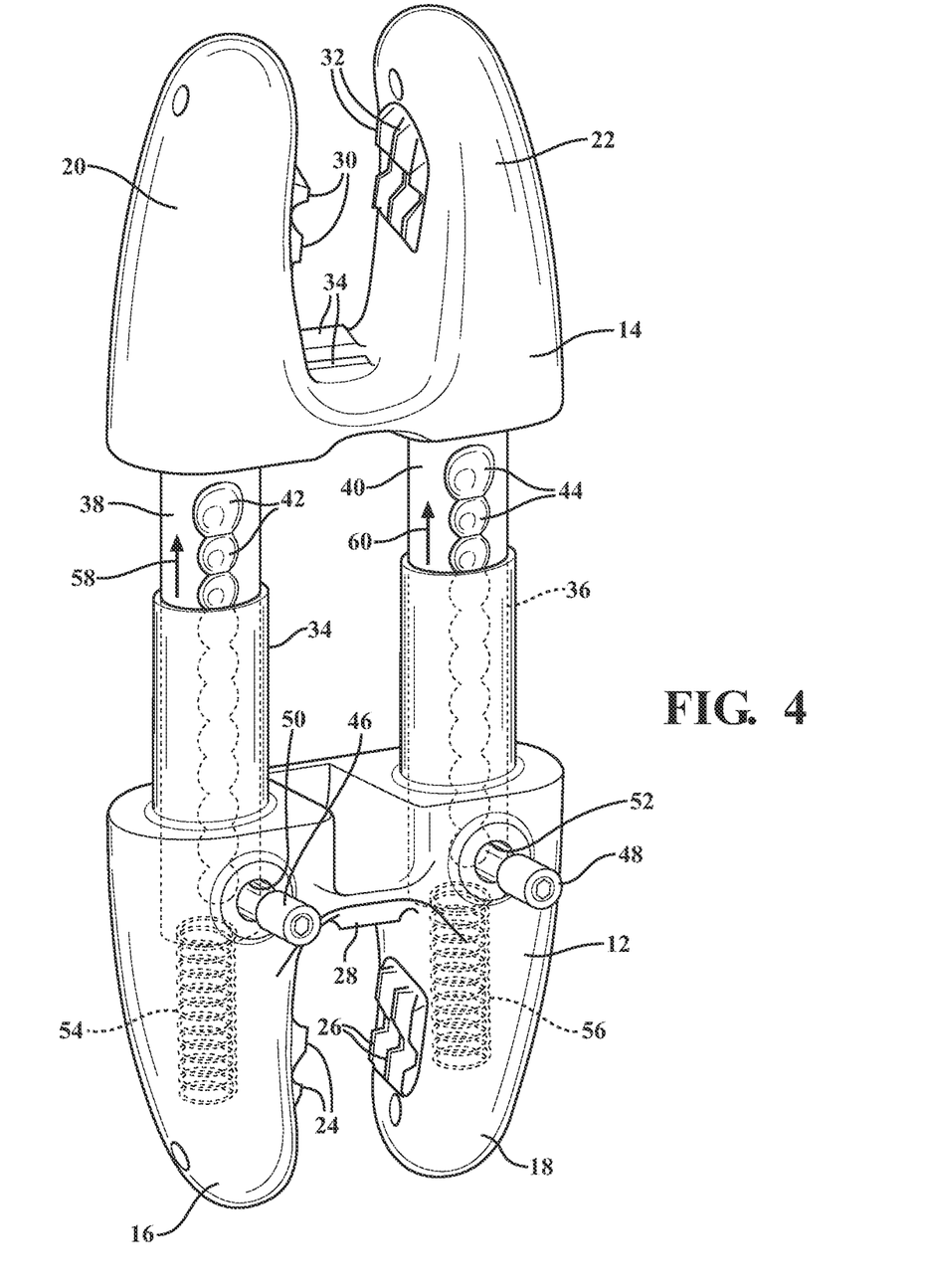
FIG. 4 is an exploded view of the spinal jack assembly and depicting the interior worm screw and gearing for separating the upper and lower halves.

As best shown in the expanded views of FIGS. 3-4, the lower jack half 12 includes a pair of sleeve shaped and upwardly extending portions 34 and 36. The upper jack half 14 further includes a pair of downwardly extending stems 38 and 40 which, as best shown in FIG. 4, are telescopically and coaxially received within the upward extending sleeve portions 34/36. Each of the stems 38/40 include an individual plurality of inwardly stepped ratchet locations (see at 42 for stem 38 and at 44 for stem 40 and which, without limitation, can be spaced at any desired incremental distance such as 2 mm per step).

A pair of spring stepped pins are shown in exploded fashion in FIG. 4 at 46 and 48, these seating through annular recesses depicted by annular inner rims 50 and 52 in a base portion of the lower spinal jack half 12. The aperture defined recesses are in communication with the ratchet locations 42/44 so that the inner ends of the spring pins 46/48 engage selected ratchet locations of the stems 38/40 to define a desired separation distance between the jack halves 12/14.

Although not shown, the spring pins 46/48 can be adjustably secured within the lower jack halves by any of opposing thread patterns. Alternatively, any type of bayonet tab and slot structure can be incorporated between the pins 46/48 and the surrounding annular inn rim surfaces 50/52 so that the spring pins can be inwardly displaced (such as via a suitable tool with bit engaging end or the like) and subsequently rotated in order to engage the stems a desired adjusted position.

As shown in phantom in FIG. 4, a pair of coil springs 54 and 56 are shown which are seated within interior pockets defined in the lower jack half 12, such that upwardly biasing ends contact and actuate the stems 38/40 and the upper jack half 14 outwardly against the supported articular processes 2 and 4 and to assist in adjusting a lateral separation between the jack halves.

In use, the spinal jack 10 is simultaneously compressed and positioned in relation to a pair of succeeding superior articular processes. Upon releasing, the jack halves 12/14 separate (see directional arrows 58/60 in FIG. 4) so that the gripping portions abut the succeeding processes 2/4 (this corresponding to each inward facing pair of stepped locations being cleared as the springs 54/56 progressively and outwardly expand the spinal jack halves 12/14, and which can occur up to a bottom most and inwardly-most stepped pair of opposing ratchets as shown in FIG. 4 in general alignment with the spring pins 46/48. Once the spinal jack halves 12/14 are progressively expanded and final adjusted to establish the desired separation distance, the spring pins 54/56 are actuated (such as again in press and twist fashion) in order to lock the jack halves in the desired spatial orientation.

Figure 5:
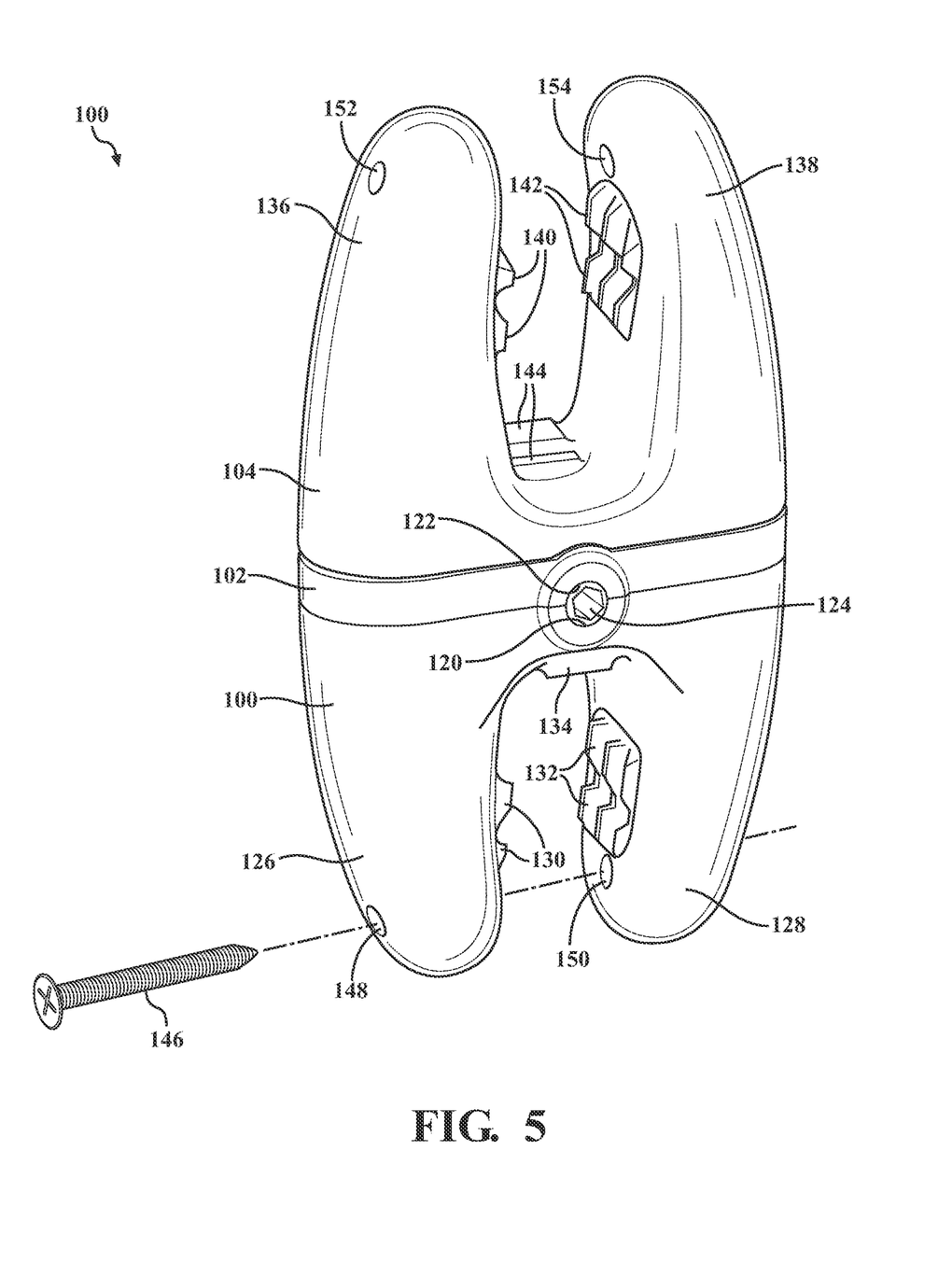
FIG. 5 is a perspective view of a further variant of jack according to a further non-limiting variant, again having first and second spinal jack halves shown in a retracted position prior to being installed between succeeding superior articular processes associated with upper and lower consecutive spinal vertebra.
Figure 6:
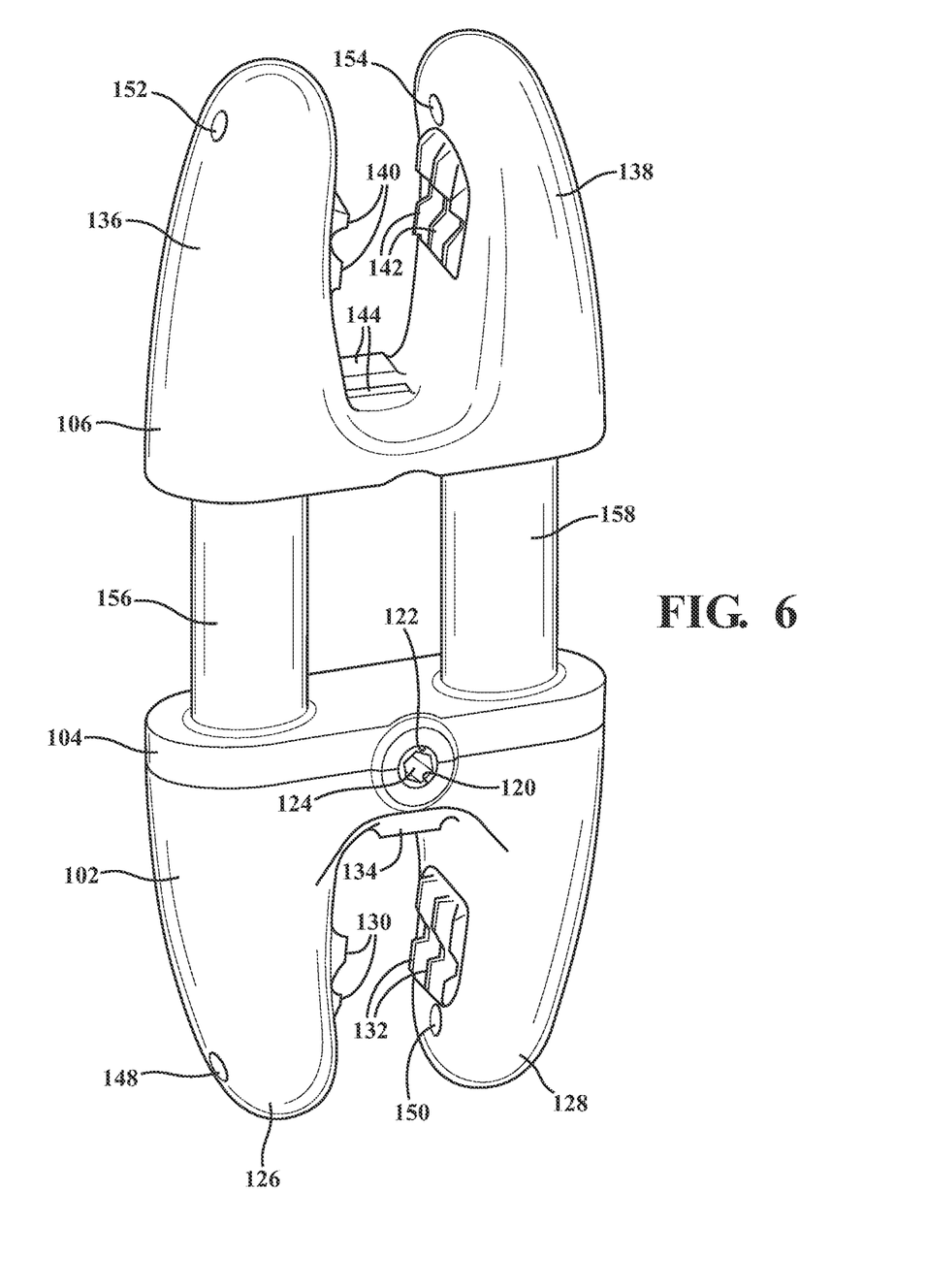
FIG. 6 illustrates an expanded position of the jack of FIG. 5.

Proceeding now to FIG. 5, a perspective view is generally shown at 100 of a spinal jack according to a further non-limiting variant in a retracted position and, similar to the variant 10 of FIG. 1, includes a three dimensional and arcuate ergonomic main body, this constructed from first 102 and second 104 subset body portions, from which is displaceable an upper body 106 (as best shown in FIG. 3). The main body 102/104 and upper displace-able body 106 are again each constructed of a suitable sanitary medical grade material not limited to any of a metal or plastic composition.

Figure 7:
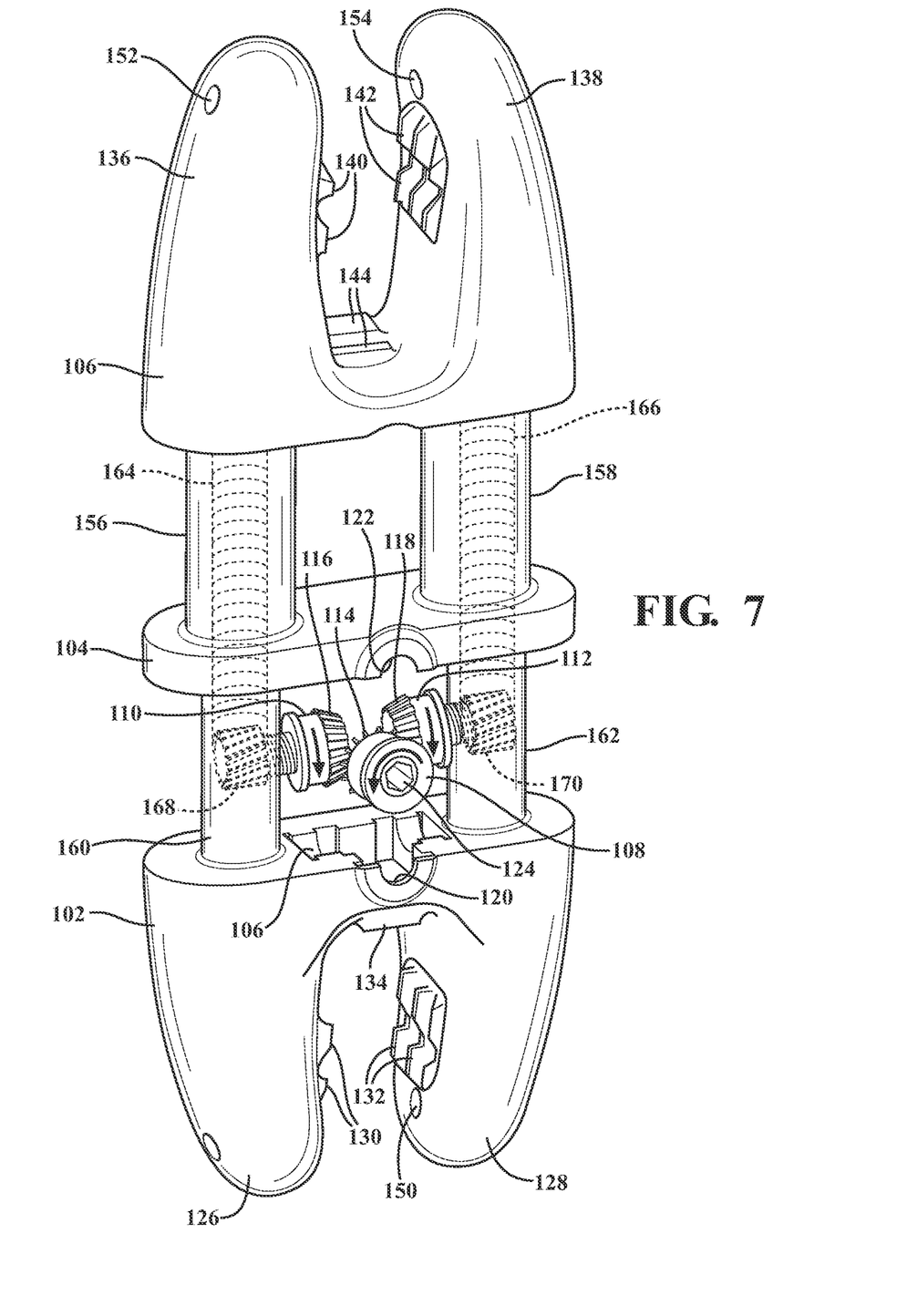
FIG. 7 is partially exploded view of the jack of FIG. 5 and depicting a gear arrangement in substitution of the spring pins of FIG. 4 for bi-directional actuation of the jack halves.

Each of the main body subset portions 102 and 104 are arranged in a mirrored opposing and abutting end face orientation. As best shown in FIG. 7, an interior recessed cavity includes aligning location formed within each opposing base (see at 106 associated with subset body portion 102), for collectively seating a central gear 108 and a pair of outer beveled and actuated gears 110/112 in a side-by-side configuration. As further shown in FIG. 7, the central gear 108 includes a spiral array of teeth 114 extending along its generally horizontal length which mesh with crosswise bevel arranged and annular gear teeth, shown at 116 arranged upon outer gear 110 and further teeth 118 arranged upon the other outer gear 112.

An inlet aperture to the central gear 108 is provided by subset rim portions 120 and 122 which are defined in aligning fashion between the opposing end faces of the subset body portions 102/104. In this fashion, a tool bit or the like (not shown) can be inserted within the inlet aperture into engagement with a central bit receiving location 124 for actuating the central gear 108 and meshing outer beveled gears 110/112. The present invention contemplates any bit configuration for rotating the central gear 108, such including without limitation a hex key profile as depicted.

Figure 2:
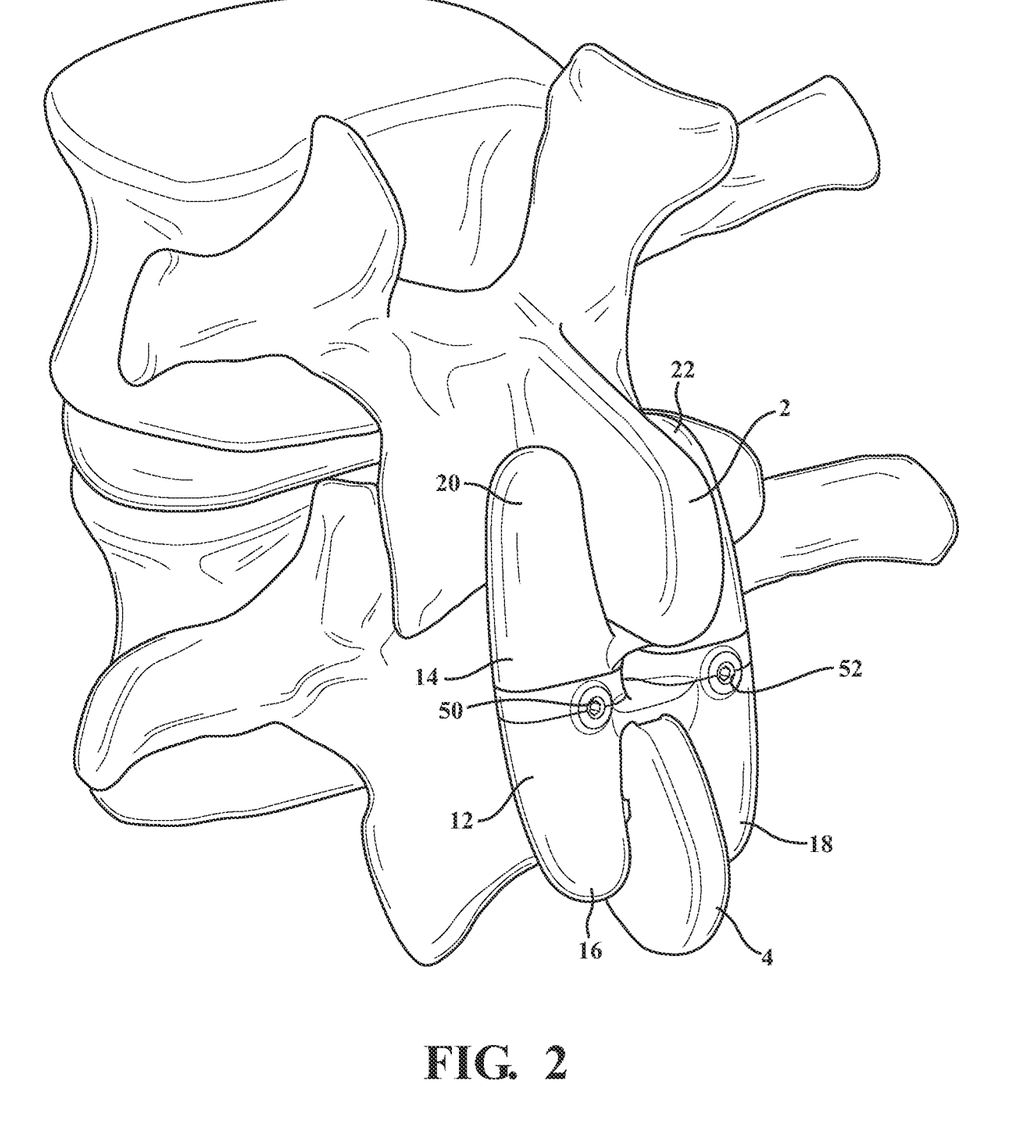
FIG. 2 is an environmental illustration of the spinal jack of FIG. 1 depicted in a retracted position installed between succeeding superior articular processes associated with upper and lower consecutive spinal vertebrae.

Each of the subset body portions 102/104 also depict inwardly contoured or recessed channels for receiving the superior articular processes 2 and 4 (depicted in FIGS. 2-3). A first lower channel is configured in the lower positioned the subset body portion 102 and is defined by a pair spaced apart extending sides 126/128, each further exhibiting opposing side surface gripping locations 130/132 and a further inside middle gripping location 134 for configuring a first superior articular process receiving pocket.

As shown, the upper body 106 includes an upper recessed channel defined by a further pair of spaced apart sides 136/138, each further exhibiting opposing side surface gripping locations 140/142 and a further inside middle gripping location 144 for configuring a second superior articular process receiving pocket. The spaced apart pairs of sides 126/128 and 136/138 of the opposite extending gripping portions are adapted to seat the upper 2 and lower 4 consecutive superior articular processes, the inner "U" shaped surface profile of each configured pocket includes each of the gripping portions being further exhibited by any type of textured or ribbed profile, the purpose of which is to provide additional resistive engagement against the facet surfaces of the processes 2 and 4.

Any type of screw fastener (such as shown at 146 in FIG. 5) is employed with each gripping portion and which, upon positioning the gripping portions and drilling through the processes 2 and 4 (in alignment with aligning pairs of apertures 148/150 and 152/154 formed through the spaced apart pairs of sides 126/128 and 136/138), provides for anchoring the lower and upper jack halves to the respective vertebrae. Alternatively, the gripping portions defining each pocket can be provided without aligning apertures (see again FIG. 1) and which can be crimped into engagement with the vertebral processes 2 and 4, such as without the use of separate screws.

As with the initial variant, the lower body can include any configuration of sleeve or fixed support, see at 156/158 extending upwardly from the lower jack (depicted as upper sub-portion 104). As shown in the exploded view of FIG. 7, a pair of intermediate sleeves can be provided at 160/162 which coaxially seat within hollow underside locations of the upper base sub-portion 104 in order to anchor the two piece lower spinal jack half together in a fashion that it integrates the gears 108, 110 and 112.

As further shown in phantom in FIG. 7, the upper body 106 includes a pair of elongated stems 164 and 166 which are anchored at upper ends to lateral locations in the upper body 106. The stems 164/166 extend downwardly and respectively seat within and through elongated interior channels or passageways defined in the coaxially arranged sleeves 156/158 and 160/162.

As further shown in FIG. 7, the stems 164/166 each further exhibit a geared or teethed profile. Rotation of the outer gears 110/112 by the central gear 108, results in additional gears (see in phantom at 168/170) located within the interior of the base support sleeves 160/162 actuating relative to the stems 164/166 in order to upwardly/downwardly displace the upper jack body 106 relative to the assembled lower jack body 102/104.

Without limitation, the gearing arrangement can be modified from that shown for translating the rotation of the central gear 108, the beveled actuation of the outer gears 110/112 and the resultant linear actuation of the upper jack body 106. This can include reconfiguration of the stem ratchets 164/166 as spiral threads of the like which coact with any alternate reconfigured arrangement of input gearing (again at 168/170) for effectuating bi-directional adjustment of the spinal jack bodies.

In this fashion, and upon pre-positioning and initial attachment of the spinal jack 100 between the succeeding superior articular processes, the tool bit is inserted through the collectively defined aperture (collectively at 120/122) and into the (hex) bit receiving recess 124 of the central gear 108 and further, upon being rotated in a selected rotational direction, results in the outer bevel configured gears 110/112 being rotated in order to elevate the stems and upper end supported spinal jack body 106. Although not shown, it is envisioned and understood that additional spinal braces and the like can be provided (not shown) which can be installed against the later processes of each vertebrae and in order to provide additional vertebral support depending upon the nature of the spinal injury being addressed.

Having described my invention, other and additional preferred embodiments will become apparent to those skilled in the art to which it pertains, and without deviating from the scope of the appended claims. The detailed description and drawings are further understood to be supportive of the disclosure, the scope of which being defined by the claims. While some of the best modes and other embodiments for carrying out the claimed teachings have been described in detail, various alternative designs and embodiments exist for practicing the disclosure defined in the appended claims.

The foregoing disclosure is further understood as not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosure. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application. Additionally, any signal hatches in the drawings/figures should be considered only as exemplary, and not limiting, unless otherwise specifically specified.

The invention claimed is:

1. A spinal jack adapted for installation between first and second vertebral processes, comprising:

an upper spinal jack body and a lower spinal jack body, each of said bodies including gripping portions adapted for engaging the vertebral processes;

a pair of upwardly extending sleeves extending upwardly from said lower spinal body and coaxially receiving a pair of stems extending downwardly from said upper spinal body so that a first end surface of said upper spinal jack body is spaced upwardly from a second end surface of said lower spinal body;

outward biasing springs seated within said lower spinal jack body in communication with said sleeves for upwardly displacing said stems and said upper spinal jack body;

inwardly actuated pins seating through annular recesses in said lower jack body and engaging recessed ratchet locations configured along an axial length of each of said stems extending within said sleeves, said inwardly actuated pins each configured to selectively engage a plurality of said ratchet locations configured along each of said stems; and said bodies being simultaneously compressed and adapted to being positioned between the vertebral processes such that, upon being released, said bodies expanding into contact with the processes and being subsequently locked by said pins in order to define an adjusted separation distance between said upper and lower bodies.

2. The spinal jack as described in claim 1, said gripping portions each further comprising a pocket adapted to receive the vertebral process there between.

3. The spinal jack of claim 2, said pockets each further comprising textured surfaces for providing additional gripping of the vertebral processes.

4. The spinal jack of claim 1, further comprising each of said upper and lower bodies further comprising any medical grade sanitary metal, plastic or composite material.

5. The spinal jack of claim 1, each of said gripping portions further comprising a substantially "U" shape with aligning apertures configured in spaced apart and extending legs for receiving screw fasteners for securing said gripping portions to the vertebral processes.

* * * * *